United States Patent [19]

Prusiner et al.

[11] Patent Number: 5,977,324
[45] Date of Patent: Nov. 2, 1999

[54] PROCESS FOR CONCENTRATING PROTEIN WITH DISEASE-RELATED CONFORMATION

[75] Inventors: Stanley B. Prusiner, San Francisco; Jiri G. Safar, Concord, both of Calif.

[73] Assignee: The Regents of the University of California, Oakland, Calif.

[21] Appl. No.: 09/026,967

[22] Filed: Feb. 20, 1998

[51] Int. Cl.$^6$ ........................................... C07K 3/00
[52] U.S. Cl. ..................... 530/418; 530/402; 530/403; 530/412; 530/413; 530/419; 530/420; 530/421; 436/536; 436/538; 436/539
[58] Field of Search ..................... 530/402, 403, 530/412, 413, 418, 419, 420, 421; 436/536, 538, 539

[56] References Cited

U.S. PATENT DOCUMENTS

| | | | |
|---|---|---|---|
| 4,806,627 | 2/1989 | Wisniewski et al. | 530/387 |
| 5,565,186 | 10/1996 | Prusiner et al. | 424/9.2 |
| 5,750,361 | 5/1998 | Prusiner et al. | 435/23 |
| 5,858,326 | 1/1999 | Kisilevsky et al. | 424/9.2 |

FOREIGN PATENT DOCUMENTS

WO 93/10227   5/1993   WIPO .

OTHER PUBLICATIONS

Anderson et al., (1996) "Transmission dynamics and epidemiology of BSE in British cattle," *Nature* 382: 779–88.

Barry, R.A., et al., (1986) "Monoclonal Antibodies to the Cellular and Scrapie Prion Proteins," *Journal of Infectious Diseases* 154:518–521.

Basler et al., (1986) "Scrapie and Cellular PrP Isoforms are Encoded by the Same Chromosomal Gene," *Cell* 46:417–28.

Bendheim, et al., (1984) "Antibodies to a Scrapie Prion Protein," *Nature* 310:418–421.

Bode et al., (1985) "Characterization of Antisera Against Scrapie-Associated Fibrils (SAF) from Affected Hamster and Cross-Reactivity with SAF from Scrapie-Affected Mice and from Patients with Creutzfeldt–Jacob Disease," *J. Gen. Virol.* 66:2471–2478.

Bolton et al., (1982) "Identification of a Protein That Purifies with the Scrapie Prion," *Science* 218:1309–11.

Brown et al., (1992) "'Friendly Fire'in Medicine: Hormones, Homografts and Creutzfeldt–Jakob Disease," *Lancet* 340:24–27.

Buchanan et al., (1991) "Mortality, Neoplasia, and Creutzfeldt–Jakob Disease in Patients Treated with Human Pituitary Growth Hormone in the United Kingdom", *BMJ* 302:824–828.

Bueler et al., (1992) "Normal Development and Behavior of Mice Lacking the Neuronal Cell–surface Prp Protein," *Nature* 356:577–582.

Carter, et al., (1992) "High Level*Escherichia coli* Expression and Production of a Bivalent Humanized Antibody Fragment," *Biotechnology* 10:163–7.

Cochius et al., (1992), "Creutafeldt–Jakob Disease in a Recipeint of Human Pituitary–Derived Gonadotrophin: A Second Case," *J. Neurol. Neurosurg. Psychiatry* 55:1094–1095.

Cochius et al., (1990) "Creutzfeldt–Jakob Disease in a Recipeint of Human Pituitary–Derived Gonadotrophin," *Aust. N.Z. J. Med.* 20:592–593.

Collinge, et al., (1996) "Prion protein gene analysis in new variant cases of Creutzfeldt–Jakob disease," *Lancet* 348:56.

Gajdusek, D.C., (1977) "Unconventional Viruses and the Origin and Disappearance of Kuru," *Science* 197:943–960.

Gibbs, Jr. et al., (1993) "Creutzfeldt–Jakob Disease Infectivity of Growth Hormone Derived from Human Pituitary Glands," *N. Engl. J. Med.* 328:358–359.

Goldfarb et al., (1992) "Fatal Familial Insomnia and Familial Creutzfeldt–Jakob Disease: Disease Phenotype Determined by a DNA Polymorphism," *Science* 258:806–808.

Healy et al., "Creutzfeldt–Jakob Disease After Pituitary Gonadotrophins: The Prion is the Problem," *BMJ* (1993) 307:517–518.

Hsiao et al., (1994) "Serial transmission in rodents of neurodegeneration from transgenic mice expressing mutant rion protein," *Proc. National Acad. Sci. USA* 91:9126–30.

Kascsak, R.J., et al., (1987) "Mouse Polyclonal and Monoclonal Antibody to Scrapie–Associated Fibril Proteins" *Journal of Virology* 61:3688–3693.

Lasmezas et al., (1993) "Recombinant Human Growth Hormone and Insulin–Like Growth Factor I Induce PRP Gene Expression in PC12 Cell," *Biochem. Biophys. Res. Commun.* 196:1163–1169.

McKinley et al., (1983) "A Protease–Resistant Protein is a Structural Component of the Scrapie Prion," *Cell* 35:57–62.

Melhorn et al., (1996) "High–Level Expression and Characterization of a Purified 142–Residue Polypeptide of the Prion Protein," *Biochemistry* 35:5528–37.

Meyer et al., (1986) "Separation and Properties of Cellular and Scrapie Prion Proteins," *Proc. Natl. Acad. Sci. USA* 83:2310–2314.

(List continued on next page.)

*Primary Examiner*—Cecilia J. Tsang
*Assistant Examiner*—Cybille Delacroix-M
*Attorney, Agent, or Firm*—Karl Bozicevic; Bozicevic, Field & Francis LLP

[57] ABSTRACT

A method of concentrating a disease-related conformation of a protein such as the PrP$^{Sc}$ in a sample is disclosed. The method comprises liquefying the sample and adding a complexing agent such as phosphotungstic acid (PTA) which complexes preferentially or exclusively with the PrP$^{Sc}$. After the complex is formed the composition is centrifuged until the complex settles at the bottom. Thereafter, the supernatant is poured away. The remaining pellet may be resuspended in an aqueous solution containing a protease inhibitor for storage. The PTA stains the PrP$^{Sc}$ making the resulting concentrated PrP$^{Sc}$ susceptible to further analysis, making it possible to quickly and efficiently determine the presence of PrP$^{Sc}$ and its concentration in a sample. The method can be used to render a sample non-infectious by removing all or substantial of the infectious form of a protein from a sample.

20 Claims, 1 Drawing Sheet

OTHER PUBLICATIONS

Oesch, et al., (1985) "A Cellular Gene Encodes Scrapie PrP 27–30 Protein," *Cell* 40:735–46.

Pan, et a., (1993) "Conversion of α–helices into β–sheets features in the formation of the scrapie prion proteins," *Proc. Natl. Acad. Sci. USA* 90:10962–66.

Pan, et al., (1992) "Purification and Properties of the Cellular Prion Protein from Syrian Hamster Brain," *Protein Sci.* 1:1343–1352.

Prusiner, S.B. et al., (1983) "Scrapie prions aggregate to form amyloid–like birefringent rods," *Cell* 35:349–58.

Prusiner, S.B. et al., "Biology of Prions," *The Molecular and Genetic Basis of Neurological Disease,* 2nd Edition, Chap. 7, pp. 103–143.

Rogers et al., (1991) "Epitope Mapping of the Syrian Hamster Prion Protein Utilizing Chimeric and Mutant Genes in a Vaccinia Virus Expression System," *J. Immunol.* 147: 3568–74.

Rogers, et al., (1993) "Conversion of truncated and elongatged prion proteins into the scrapie isoform in cultured cells," *Proc. Natl. Acad. Sci. USA* 90:3182–6.

Safar et al. J., (1993) "Conformational Transitions, Dissociation, and Unfolding of Scrapie Amyloid (Prion) Protein," *J. Biol. Chem.* 268: 20276–84.

Safar, et al., (1990) "Scrapie–associated precursor proteins: Antigenic relationship between species and immunocytochemical localization in normal, scrapie, and Creutzfeldt–Jakob disease brains," *Neurology* 40:513–7.

Serban et al, (1990) "Rapid Detection of Creuzfeldt–Jakob Disease and Scrapie Prion Proteins," *Neurology* 40:110–7.

Stahl et al., (1993) "Structural Studies of the Scrapie Prion Protein Using Mass Spectrometry and Amino Acid Sequencing," *Biochemistry* 32:1991–2002.

Taraboulos et al., (1992) "Regional Mapping of Prion Proteins in Brain," *Proc. Natl. Acad. Sci. USA* 89:7620–7624.

Turk, et al., (1988) "Purification and Properties of the Cellular and Scrapie Hamster Prion Proteins," *Eur. J. Biochem.* 176:21–30.

Wilesmith and Wells, (1991) "Bovine Spongiform Encephalopathy," *Curr. Topics Microbiol. Immunol.* 172 21–38.

Wilesmith, "Bovine Spongiform Encephalopathy," *Methods in Molecular Medicines: Prion Diseases,* pp. 155–73.

Williamson, et al., (1996) "Circumventing tolerance to generate autologous monoclonal antibodies to the prion protein," *Proc. Natl. Acad. Sci. USA* 93:7279–82.

Figure 1

PROCESS FOR CONCENTRATING PROTEIN WITH DISEASE-RELATED CONFORMATION

FIELD OF THE INVENTION

This invention relates generally to methods of treating proteins and more specifically to methods of concentrating a particularly desired protein within a sample.

BACKGROUND OF THE INVENTION

Prions are infectious pathogens that cause invariably fatal prion diseases (spongiform encephalopathies) of the central nervous system in humans and animals. Prions differ significantly from bacteria, viruses and viroids. The dominating hypothesis is that no nucleic acid is necessary to allow for the infectivity of a prion protein to proceed.

A major step in the study of prions and the diseases they cause was the discovery and purification of a protein designated prion protein [Bolton, McKinley et al. (1982) *Science* 218:1309–1311; Prusiner, Bolton et al. (1982) *Biochemistry* 21:6942–6950; McKinley, Bolton et al. (1983) *Cell* 35:57–62]. Complete prion protein-encoding genes have since been cloned, sequenced and expressed in transgenic animals. $PrP^c$ is encoded by a single-copy host gene [Basler, Oesch et al. (1986) *Cell* 46:417–428] and when $PrP^c$ is expressed it is generally found on the outer surface of neurons. Many lines of evidence indicate that prion diseases results from the transformation of the normal form of prion protein ($PrP^c$) into the abnormal form ($PrP^{Sc}$). There is no detectable difference in the amino acid sequence of the two forms. However, $PrP^{Sc}$ when compared with $PrP^c$ has a conformation with higher β-sheet and lower α-helix content [Pan, Baldwin et al. (1993) *Proc Natl Acad Sci USA* 90:10962–10966; Safar, Roller et al. (1993) *J Biol Chem* 268:20276–20284]. The presence of the abnormal $PrP^{Sc}$ form in the brains of infected humans or animals is the only disease-specific diagnostic marker of prion diseases.

$PrP^{Sc}$ plays a key role in both transmission and pathogenesis of prion diseases (spongiform encephalopathies) and it is a critical factor in neuronal degeneration [Prusiner (1997) The Molecular and Genetic Basis of Neurological Disease, 2nd Edition: 103–143]. The most common prion diseases in animals are scrapie of sheep and goats and bovine spongiform encephalopathy (BSE) of cattle [Wilesmith and Wells (1991) *Curr Top Microbiol Immunol* 172:21–38]. Four prion diseases of humans have been identified: (1) kuru, (2) Creutzfeldt-Jakob Disease (CJD), (3) Gerstmann-Streussler-Sheinker Disease (GSS), and (4) fatal familial insomnia (FFI) [Gajdusek (1977) *Science* 197:943–960; Medori, Tritschler et al. (1992) N Engl J Med 326:444–449]. Initially, the presentation of the inherited human prion diseases posed a conundrum which has since been explained by the cellular genetic origin of PrP.

Most CJD cases are sporadic, but about 10–15% are inherited as autosomal dominant disorders that are caused by mutations in the human PrP gene [Hsiao and Prusiner (1990) *Neurology* 40:1820–1827; Goldfarb, Petersen et al. (1992) *Science* 258:806–808; Kitamoto and Tateishi (1994) *Philos Trans R Soc Lond B* 343:391–398]. However, the human prion diseases are also infectious; the first recognized example being kuru which is believed to spread in New Guinea highlands by ritualistic cannibalism. Another example of human-to-human transmission are cases of iatrogenic CJD, caused by human growth hormone derived from cadaveric pituitaries as well as dura mater grafts [Brown, Preece et al. (1992) *Lancet* 340:24–27]. A newly perceived threat of human infection arises in the recent cases of variant CJD with the possible transmission of prions from BSE-infected cows. The seriousness of the health risk resulting from the lack of a direct prion assays in different body fluids, tissue samples or human- and animal-derived pharmaceuticals is exemplified below.

More than 75 young adults who were previously treated with (HGH) human growth hormone derived from human pituitaries have developed CJD [Koch, Berg et al. (1985) *N Engl J Med* 313:731–733; Buchanan, Preece et al. (1991) *Br Med J* 302:824–828; Fradkin, Schonberger et al. (1991) *JAMA* 265:880–884; Brown, Preece et al. (1992) *Lancet* 340:24–27]. Fortunately, recombinant HGH is now used, although the seemingly remote possibility has been raised that increased expression of wild-type $PrP^c$ stimulated by high HGH might induce prion disease [Lasmézas, Deslys et al. (1993) *Biochem Biophys Res Commun* 196:1163–1169]. The conclusion that the HGH prepared from pituitaries was contaminated with prions, is supported by the transmission of prion disease to a monkey 66 months after inoculation with a suspect lot of HGH [Gibbs, Asher et al. (1993) *N Engl J Med* 328:358–359]. Because of the long incubation times associated with prion diseases it will not be possible to determine the full extent of iatrogenic CJD in thousand of people treated with HGH worldwide for decades. Iatrogenic CJD also appears to have developed in four infertile women treated with contaminated human pituitary-derived gonadotropin hormone [Cochius, Mack et al. (1990) *Aust N Z J Med* 20:592–593; Cochius, Hyman et al. (1992) *J Neurol Neurosurg Psychiatry* 55:1094–1095; Healy and Evans (1993) *Br J Med* 307:517–518] as well as at least 11 patients receiving dura mater grafts [Thadani, Penar et al. (1988) *J Neurosurg* 69:766–769; Nisbet, MacDonaldson et al. (1989) *J Am Med Assoc* 261:1118; Willison, Gale et al. (1991) *J Neurol Neurosurg Psychiatry* 54:940; Brown, Preece et al. (1992) *Lancet* 340:24–27]. These cases of iatrogenic CJD underscore the need to screen pharmaceuticals that might possibly be contaminated with prions.

Recently, two physicians in France were charged with involuntary manslaughter of a child who had been treated with growth hormones extracted from corpses. The child developed Creutzfeldt-Jakob Disease (see *New Scientist, Jul.* 31, 1993, page 4). According to the Pasteur Institute, since 1989 there have been 24 reported cases of CJD in young people who were treated with human growth hormone between 1983 and mid-1985. Fifteen of these children have died. It appears that hundreds of children in France have been treated with growth hormone extracted from dead bodies that were at risk for developing CJD (see *New Scientist, Nov.* 20, 1993, page 10).

Another major concern is the epidemic of BSE in Great Britain and additional cases in some other countries of European Community [Wilesmith (1996) Methods in Molecular Medicine: Prion Diseases: 155–173]. The epidemic spread in the early 80s was probably due to the recycling of prion-infected animals in the rendering process and the feeding of cattle with prion-contaminated protein supplement. The enormous economic cost of eradication of BSE, if ever completely possible [Anderson, Donnelly et al. (1996) *Nature* 382:779–788], is now outweighed by the discovery of new variant CJD in young people in Great Britain which was probably transmitted by consumption of BSE-contaminated beef [Collinge, Beck et al. (1996) *Lancet* 348:56; Collinge, Sidle et al. (1996) *Nature* 383:685–690; Will, Ironside et al. (1996) *Lancet* 347:921–925]. Because of the long incubation time of CJD, it is too early to estimate the true extent of threat to the general population in Great Britain and the rest of the Europe from the available epidemiology. The BSE epidemic in cows, the "new variant" CJD and all the cases of iatrogenic CJD in young people underscore the need for screening food sources and pharmaceuticals that might possibly be contaminated with prions.

The most sensitive method today to detect and measure prions is bioassay in transgenic animals overexpressing the cellular prion protein $PrP^c$. The current prion titrations are performed in two steps: (1) the sample material is first injected into susceptible experimental animals to amplify prions and $PrP^{Sc}$ protein to detectable levels; (2) the clinically symptomatic animals are euthanized and the disease is verified by detecting disease-specific $PrP^{Sc}$ and pathology. Since the discovery of protease resistance of $PrP^{Sc}$ more than 15 years ago, the $PrP^{Sc}$ detection is exclusively based on protease treatment of brain samples with proteinase K; the residual C-terminal protease-resistant fragment PrP 27–30 is then detected in denatured form by polyclonal or monoclonal antibodies recognizing prion protein on Western blots. More recent modifications of the same principle are semiquantitative dot blots or qualitative histoblots [Serban, Taraboulos et al. (1990) Neurology 40:110–117; Taraboulos, Jendroska et al. (1992) Proc Natl Acad Sci USA 89:7620–7624].

Despite the dramatic shortening of incubation time of human prions in transgenic mice overexpressing chimeric or human PrP genes, in some cases to less than 120 days, the potential for broad and high flow-through application of such prion bioassays is still limited. One possibility further shortening the assay time is to increase the sensitivity of $PrP^{Sc}$ detection. This would shorten the necessary observation time, increase the flow-through and as a result, make assays less expensive and broadly applicable.

A system for detecting $PrP^{Sc}$ by enhancing immunoreactivity after denaturation is provided in Serban, et al., Neurology, Vol. 40, No. 1, Ja 1990. Sufficiently sensitive and specific direct assay for infectious $PrP^{Sc}$ in biological samples could potentially abolish the need for animal inoculations completely. Unfortunately, such does not appear to be possible with current $PrP^{Sc}$ assays—it is estimated that the current sensitivity limit of proteinase-K and Western blot-based $PrP^{Sc}$ detection is in a range of 1 µg/ml which corresponds to $10^4$–$10^5$ prion infectious units. Additionally, the specificity of the traditional proteinase-K-based assays for $PrP^{Sc}$ is in question in light of recent findings of only relative or no proteinase-K resistance of undoubtedly infectious prion preparations [Hsiao, Groth et al. (1994) Proc Natl Acad Sci USA 91:9126–9130] Telling, et al. (1996) Genes & Dev.

Human transthyretin (TTR) is a normal plasma protein composed of four identical, predominantly β-sheet structured units, and serves as a transporter of hormone thyroxin. Abnormal self assembly of TTR into amyloid fibrils causes two forms of human diseases, namely senile systemic amyloidosis (SSA) and familial amyloid polyneuropathy (FAP) [Kelly (1996) Curr Opin Strut Biol 6(1):11–7]. The cause of amyloid formation in FAP are point mutations in the TTR gene; the cause of SSA is unknown. The clinical diagnosis is established histologically by detecting deposits of amyloid in situ in bioptic material.

To date, little is known about the mechanism of TTR conversion into amyloid in vivo. However, several laboratories have demonstrated that amyloid conversion may be simulated in vitro by partial denaturation of normal human TTR [McCutchen, Colon et al. (1993) Biochemistry 32(45) :12119–27; McCutchen and Kelly (1993) Biochem Biophys Res Commun 197(2) 415–21]. The mechanism of conformational transition involves monomeric conformational intermediate which polymerizes into linear β-sheet structured amyloid fibrils [Lai, Colon et al. (1996) Biochemistry 35(20):6470–82]. The process can be mitigated by binding with stabilizing molecules such as thyroxin or triiodophenol [Miroy, Lai et al. (I1996) Proc Natl Acad Sci USA 93(26) :15051–6].

In view of the above points, there is clearly a need for a specific, high flow-through, and cost-effective assay for testing sample materials for the presence of infectious form of prion protein, $PrP^{Sc}$, which is believed to be the cause of prion diseases, such as BSE, CJD and scrapie. The presented invention offers a method of improving sensitivity of a range of different assays.

SUMMARY OF THE INVENTION

A method of concentrating a disease conformation of a protein such as the $PrP^{Sc}$ in a sample is disclosed. The method comprises liquefying the sample and adding a complexing agent such as phosphotungstic acid (PTA) which complexes with the $PrP^{Sc}$. After the complex is formed the composition is centrifuged until the complex settles at the bottom. Thereafter, the supernatant is poured away. The remaining pellet may be resuspended in an aqueous solution containing a protease inhibitor for storage. The PTA stains the $PrP^{Sc}$ making the resulting concentrated $PrP^{Sc}$ susceptible to further analysis. The original sample has been cleansed of $PrP^{Sc}$ to the extent that a sample originally possessing infectivity is rendered non-infective.

An object of the invention is to provide a method for concentrating the disease conformation of a protein which has two or more conformational forms.

A specific object of the invention is to provide a method for concentrating $PrP^{Sc}$ within a sample.

Another object is to reduce or completely eliminate the infectivity of a sample as regards prion diseases.

An advantage of the invention is that it can be quickly and conveniently carried out without the use of complex procedures or devices.

Another advantage is that materials containing infective amounts of $PrP^{Sc}$ can be rendered non-infective.

A feature of the invention is that $PrP^{Sc}$ forms complexes almost exclusively with phosphotungstic acid.

An important object of the method is to concentrate infectious prions present from crude mixtures such as brain homogenates or in variable sample materials obtained or derived from human, primate, monkey, hamster, mice, pig, bovine, sheep, deer, elk, cat, dog, and chicken tissues.

Another object is to provide a simple, fast, and inexpensive method to improve the safety of biologicals by eliminating infectious prions from samples potentially contaminated with prions.

Another object is to provide materials such as organic polymers, inorganic salt complexes, or metals modified by phosphotungstic acid which materials are useful in concentrating or eliminating prions from such crude mixtures.

An important feature and advantage of the method is the rapid, cost-effective and high-through design with the capacity to process more than 100 samples per day per skilled person.

These and other objects, advantages and features of the invention will become apparent to those skilled in the art upon reading this disclosure.

DETAILED DESCRIPTION OF THE PREFERRED EMBODIMENTS

Before the present assays and methods are disclosed and described, it is to be understood that this invention is not limited to particular complexing agents, proteins, labels, assays or method as such may, of course vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for the disclosure prior to the filing date of the present application. Nothing herein is to be construed as an admission that the present invention is not entitled to antedate such publication by virtue of prior invention. Further, the dates of publication provided are subject to change if it is found that the actual date of publication is different from that provided here.

DEFINITIONS

The term "complexing agent" is used herein to refer to any material which binds or complexes selectively with the constrictive conformation of a protein (e.g. with $PrP^{Sc}$) and not with the relaxed conformation of a protein (e.g. $PrP^{c}$). The resulting complex has a higher density than either the constrictive conformation or the complexing agent alone. A preferred complexing agent for $PrP^{Sc}$ is phosphotungstic acid (PTA), which may be added in the form of a salt, e.g. sodium phosphotungstate. The complexing agent preferably forms a complex which has a higher density than the density of the constricted conformation of the protein by itself. This makes it possible to precipitate the complex out by centrifugation. The complex formed must provide some means for separating the complex from the remainder of the composition.

The term "protein" as used herein is intended to encompass any amino acid sequence and include modified sequences such as glycoproteins. The term includes naturally occurring proteins and peptides as well as those which are recombinantly or synthetically synthesized. As used in connection with the present invention the term "protein" is specifically intended to cover naturally occurring proteins which occur in at least two different conformations, a "constricted conformation" and a "relaxed conformation," wherein both conformations have the same or substantially the same amino acid sequence but have different three dimensional structures. The two conformations of the protein may include at least one conformation which is not related to a disease state and at least one conformation which is related to a disease state. A specific and preferred example of a protein as used in connection with this disclosure is a PrP protein which includes a relaxed conformation (the non-disease form), referred to as $PrP^{c}$, and the constricted conformation (the disease related form), referred to as $PrP^{Sc}$.

The terms "treating", "treatment" and the like are used interchangeably here to describe a process whereby a sample or portion thereof and specifically proteins in the sample are physically and/or chemically manipulated so that proteins in the sample in a disease related conformation are caused to changed to a different conformation with higher affinity for a binding partner, e.g., a higher antibody binding affinity. Treated proteins are also referred to as denatured proteins or proteins in a relaxed conformation which conformation increases the antibody binding affinity of the protein. Treating includes subjecting the sample to heat, pressure and/or chemicals. In a preferred embodiment, samples containing $PrP^{Sc}$ (which is the disease-related conformation comprising β-sheet structural configurations) are treated so that the $PrP^{Sc}$ protein assumes a different conformation (e.g., comprising an α-helical configuration and/or a random coil configuration) having four times or more greater antibody binding affinity.

The terms "PrP protein", "PrP" and like are used interchangeably herein and shall mean both the infectious particle form $PrP^{Sc}$ known to cause diseases (spongiform encephalopathies) in humans and animals and the noninfectious form $PrP^{c}$ which, under appropriate conditions is converted to the infectious $PrP^{Sc}$ form.

The terms "prion", "prion protein" and "$PrP^{Sc}$ protein" and the like we used interchangeably herein to refer to the infectious $PrP^{Sc}$ form of a PrP protein, and is a contraction of the words "protein" and "infection." Particles are comprised largely, if not exclusively, of $PrP^{Sc}$ molecules encoded by a PrP gene. Prions are distinct from bacteria, viruses and viroids. Known prions infect animals to cause scrapie, a transmissible, degenerative disease of the nervous system of sheep and goats, as well as bovine spongiform encephalopathy (BSE), or "mad cow disease", and feline spongiform encephalopathy of cats. Four prion diseases known to affect humans are (1) kuru, (2) Creutzfeldt-Jakob Disease (CJD), (3) Gerstmann-Straussler-Scheinker Disease (GSS), and (4) fatal familial insomnia (FFI). As used herein "prion" includes all forms of prions causing all or any of these diseases or others in any animals used—and in particular in humans and domesticated farm animals.

The term "PrP gene" is used herein to describe genetic material which expresses proteins including known polymorphisms and pathogenic mutations. The term "PrP gene" refers generally to any gene of any species which encodes any form of a prion protein. Some commonly known PrP sequences are described in Gabriel et al., *Proc. Natl. Acad. Sci. USA* 89:9097–9101 (1992) and U.S. Pat. No. 5,565,186, incorporated herein by reference to disclose and describe such sequences. The PrP gene can be from any animal, including the "host" and "test" animals described herein and any and all polymorphisms and mutations thereof, it being recognized that the terms include other such PrP genes that are yet to be discovered. The protein expressed by such a gene can assume either a $PrP^{c}$ (non-disease) or $PrP^{Sc}$ (disease) form.

The terms "standardized prion preparation", "prion preparation", "preparation" and the like are used interchangeably herein to describe a composition obtained from the brain tissue of mammals which exhibits signs of prion disease: the mammal either (1) include a transgene as described herein; (2) have and ablated endogenous prion protein gene; (3) have a high number of prion protein gene from a genetically diverse species; or (4) are hybrids with an ablated endogenous prion protein gene and a prion protein gene from a genetically diverse species. Different combinations of 1–4 are possible, e.g., 1 and 2. The mammals from which standardized prion preparations are obtained exhibit clinical signs of CNS dysfunction as a result of inoculation with prions and/or due to developing the disease of their genetically modified make up, e.g., high copy number of prion protein genes.

The term "artificial PrP gene" is used to encompass the term "chimeric PrP gene" as well as other recombinantly constructed genes which, when included in the genome of a host animal (e.g. a mouse, will render the mammal susceptible to infection from prions which naturally only infect a genetically diverse test animal, e.g. human, bovine or ovine. In general, an artificial gene will include the codon sequence of the PrP gene of the mammal being genetically altered with one or more (but not all, and generally less than 40) codons of the natural sequence being replaced with a different codon—preferably a corresponding codon of a genetically diverse mammal (such as a human). The genetically altered mammal being used to assay samples for prions only affect the genetically diverse mammal. Examples of artificial genes are mouse PrP genes encoding the sequence for human, cows and sheep and replacing mouse codons at the same relative positions, with the provision that not all the mouse codons are replaced with differing human, cow or sheep codons. Artificial PrP genes can include not only codons of genetically diverse animals but may include codons and codon sequences not associated with any native PrP gene but which, when inserted into an animal render the animal susceptible to infection with prions which would normally only infect an genetically diverse animal.

The terms "chimeric gene", "chimeric PrP gene", "chimeric prion protein gene" and the like are used interchangeably herein to refer to an artificially constructed gene containing the codons of a host animal such as a mouse with one or more of the codons replaced with corresponding codons from a genetically diverse test animal such as a human, cow or sheep. In one specific example, the chimeric gene is comprised of the starting and terminating sequence (e.g.,—and C- terminal codons) of PrP gene of a mammal of host species (e.g. a mouse) and also containing a nucleotide sequence of a corresponding portion of a PrP gene of a test mammal of a second species (e.g. a human). When a chimeric gene is inserted into the genome of the host species, it will render the mammal susceptible to infection with prions which normally infect only mammals of the second species. The preferred chimeric gene disclosed herein is MHu2M which contains the starting and terminating sequence of a mouse PrP gene and a non-terminal sequence region which is replaced with a corresponding human sequence differing from a mouse PrP gene at nine residues.

The term "genetic material related to prions" is intended to cover any genetic material which affects the ability of an animal to become infected with prions. Thus the term encompasses any "PrP gene", "artificial PrP gene", "chimeric PrP gene" or "ablated PrP gene" which terms are defined herein as well as modification of such which effect the ability of an animal to become infected with prions. Standardized prion preparations are produced using animals which all have substantially the same genetic material related to prions so that all of the animals will become infected with the same type of prions and will exhibit signs of infection at approximately the same time.

The term "host animal" and "host mammal" are used to describe animals which will have their genome genetically and artificially manipulated so as to include genetic material which is not naturally present within the animal. For example, host animals include mice, hamsters and rats which have their PrP gene ablated, i.e., rendered inoperative. The host is inoculated with prion proteins to generate antibodies. The cells producing the antibodies are a source of genetic material for making a phage library. Other host animals may have a natural (PrP) gene, or one which is altered by the insertion of an artificial gene or by the insertion of a native PrP gene of a genetically diverse test animal.

The term "test animal" and "test mammal" are used to describe the animal which is genetically diverse from the host animal in terms of differences between the PrP gene of the host animal and the PrP gene of the test animal. The test animal may be any animal for which one wishes to run an assay test to determine whether a given sample contains prions with which the test animal would generally be susceptible to infection. For example, the test animal may be a human, cow, sheep, pig, horse, cat, dog or chicken, and one may wish to determine whether a particular sample includes prions which would normally only infect the test animal.

The terms "genetically diverse animal" and "genetically diverse mammal" are used to describe an animal which includes a native PrP codon sequence of the host animal which differs from the genetically diverse test animal by 17 or more codons, preferably 2 or more codons, and most preferably 28–40 codons. Thus, a mouse PrP gene is genetically diverse with respect to the PrP gene of a human, cow or sheep, but is not genetically diverse with respect to the PrP gene of a hamster.

The term "ablated PrP protein gene", "disrupted PrP gene", and the like are used interchangeably herein to mean an endogenous PrP gene which has been altered (e.g., add and/or remove nucleotides) in a manner so as to render the gene inoperative. Examples of non-functional PrP genes and methods of making such are disclosed in Büeler, H., et al "Normal development of mice lacing the neuronal cell-surface PrP protein" *Nature* 356:577–582 (1992) and Weissmann (WO93/10227). The methodology for ablating a gene is taught in Capecchi, *Cell* 51:503–512 (1987), all of which are incorporated herein by reference. Preferably both alleles of the genes are disrupted as represented by $PrP^{0/0}$ or $Prnp^{0/0}$.

The terms "hybrid animal", "transgenic hybrid animal" and the like are used interchangeably herein to mean an animal obtained by the cross-breeding of a first animal having an ablated endogenous prion protein gene with a second animal which includes either (1) a chimeric gene or artificial PrP gene or (2) a PrP gene from a genetically diverse animal. For example a hybrid mouse is obtained by cross-breeding a mouse containing an ablated mouse gene with a mouse containing (1) human PrP genes (which may be present in high copy numbers) or (2) chimeric genes. The term hybrid includes any offspring of a hybrid including inbred offspring of two hybrids provided the resulting offspring is susceptible to infection with prions with normal infect only a genetically diverse species. A hybrid animal can be inoculated with prions and serve as a source of cells for the creation of hybridomas to make monoclonal antibodies of the invention.

The terms "susceptible to infection" and "susceptible to infection by prions" and the like are used interchangeably herein to describe a transgenic or hybrid test animal which develops a disease if inoculated with prions which would normally only infect a genetically diverse test animal. The terms are used to describe a transgenic or hybrid animal such as a transgenic mouse Tg(MHu2M) which, without the chimeric PrP gene, would not come infected with a human prion but with the chimeric gene is susceptible to infection with human prions.

The term "non-infectious" means that the treated material does not cause infection. More specifically, a material is infectious if it contains sufficient amounts of PrP$^{Sc}$ such that when it is used to innoculate an animal that animal will become ill with a prion disease and would not have become ill but for the innoculation. If that material is treated per the present invention, sufficient PrP$^{Sc}$ can be removed such that the material would not cause a prion disease if used to innoculate an animal and as such has been rendered "non-infectious."

The term "antibody" stands for an immunoglobulin protein which is capable of binding an antigen. Antibody as used herein is meant to include the entire antibody as well as any antibody fragments (e.g. F(ab)', Fab, Fv) capable of binding the epitope, antigen or antigenic fragment of interest. Preferred antibodies for assays of the invention are immunoreactive or immunospecific for and therefore specifically and selectively bind to a protein of interest e.g., an A4β amyloid protein or a PrP protein. Antibodies which are immunoreactive and immunospecific for both the native non-disease form and the treated disease form but not for the untreated disease form, (e.g., for both native PrP$^c$ and treated PrP$^{Sc}$ but not native PrP$^{Sc}$) are preferred. Antibodies for PrP are preferably immunospecific—e.g., not substantially cross-reactive with related materials. Some specific antibodies which can be used in connection with the invention are disclosed in published PCT application WO 97/10505 which is incorporated herein by reference to disclose and describe antibodies. This published PCT application corresponds to U.S. Ser. No. 08/713,939 also incorporated herein by reference. Antibodies disclosed in the PCT application which selectively bind PrP$^{Sc}$ should not be used in the present invention. The term "antibody" encompasses all types of antibodies, e.g. polyclonal, monoclonal, and those produced by the phage display methodology. Particularly preferred antibodies of the invention are antibodies which have a relatively high degree of affinity for both native PrP$^c$ and treated PrP$^{Sc}$ but a relatively low degree of or substantially no binding affinity for PrP$^{Sc}$. More specifically, antibodies of the invention preferably have four times or more, more preferably fifteen times or more, and still more preferably 30 times or more binding affinity for both native PrP$^c$ and denatured PrP$^{Sc}$ as compared with the binding affinity for native PrP$^{Sc}$.

"Purified antibody" refers to that which is sufficiently free of other proteins, carbohydrates, and lipids with which it is naturally associated. Such an antibody "preferentially binds" to a treated or denatured disease conformation of a protein such as the β-sheet conformation of A4β or PrP$^{Sc}$ protein (or an antigenic fragment thereof), and does not substantially recognize or bind to other antigenically unrelated molecules. A purified antibody of the invention is preferably immunoreactive with and immunospecific for a specific species and more preferably immunospecific for native PrP$^c$ and for treated or denatured forms of PrP$^c$ and PrP$^{Sc}$ but not for native or untreated PrP$^{Sc}$.

"Antigenic fragment" of a protein (e.g., a PrP protein) is meant a portion of such a protein which is capable of binding an antibody.

By "binds specifically" is meant high avidity and/or high affinity binding of an antibody to a specific polypeptide e.g., epitope of a protein, e.g., a PrP$^c$ or A4β protein. Antibody binding to its epitope on this specific polypeptide is preferably stronger than binding of the same antibody to any other epitope, particularly those which may be present in molecules in association with, or in the same sample, as the specific polypeptide of interest e.g., binds more strongly to epitope fragments of a protein such as PrP$^{Sc}$ so that by adjusting binding conditions the antibody binds almost exclusively to an epitope site or fragments of a desired protein such as an epitope fragment exposed by treatment of PrP$^{Sc}$ and not exposed on native untreated PrP$^{Sc}$.

By "detectably labeled antibody", "detectably labeled anti-PrP" or "detectably labeled anti-PrP fragment" is meant an antibody (or antibody fragment which retains binding specificity), having an attached detectable label. The detectable label is normally attached by chemical conjugation, but where the label is a polypeptide, it could alternatively be attached by genetic engineering techniques. Methods for production of detectably labeled proteins are well known in the art. Detectable labels known in the art, but normally are radioisotopes, fluorophores, paramagnetic labels, enzymes (e.g., horseradish peroxidase), or other moieties or compounds which either emit a detectable signal (e.g., radioactivity, fluorescence, color) or emit a detectable signal after exposure of the label to its substrate. Various detectable label/substrate pairs (e.g., horseradish peroxidase/diaminobenzidine, avidin/streptavidin, luciferase/luciferin), methods for labeling antibodies, and methods for using labeled antibodies are well known in the art (see, for example, Harlow and Lane, eds. (Antibodies: A Laboratory Manual (1988) Cold Spring Harbor Laboratory Press, Cold Spring Harbor, N.Y.). Europium is a particularly preferred label.

Abbreviations used herein include:

CNS for central nervous system;

BSE for bovine spongiform encephalopathy;

CJD for Creutzfeldt-Jacob Disease;

FFI for fatal familial insomnia;

GSS for Gerstamnn-Strassler-Scheinker Disease;

Hu for human;

HuPrP for human prion protein;

Mo for mouse;

MoPrP for mouse prion protein;

SHa for a Syrian hamster;

SHaPrP for a Syrian hamster prion protein;

Tg for transgenic;

Tg(SHaPrP) for a transgenic mouse containing the PrP gene of a Syrian hamster;

Tg(HuPrP) for transgenic mice containing the complete human PrP gene;

Tg(ShPrP) for transgenic mice containing the complete sheep PrP gene;

Tg(BoPrP) for transgenic mice containing the complete cow PrP gene;

PrP$^{Sc}$ for the scrapie isoform of the prion protein;

PrP$^c$ for the cellular contained common, normal isoform of the prion protein;

MoPrP$^{Sc}$ for the scrapie isoform of the mouse prion protein;

MHu2M for a chimeric mouse/human PrP gene wherein a region of the mouse PrP gene is replaced by a corresponding human sequence which differs from mouse PrP at 9 codons;

Tg(MHu2M) mice are transgenic mice of the invention which include the chimeric MHu2M gene;

MHu2MPrP$^{Sc}$ for the scrapie isoform of the chimeric human/mouse PrP gene;

PrP$^{CJD}$ for the CJD isoform of a PrP protein;

Prnp$^{0/0}$ for ablation of both alleles of an endogenous prion protein gene, e.g., the MoPrP gene;

Tg(SHaPrP$^{+/0}$)81/Prnp$^{0/0}$ for a particular line (81) of transgenic mice expressing SHaPrP, +/0 indicates heterozygous;

Tg(HuPrP)/Prnp$^{0/0}$ for a hybrid mouse obtained by crossing a mouse with a human prion protein gene (HuPrP with a mouse with both alleles of the endogenous prion protein gene disrupted;

Tg(MHu2M)/Prnp$^{0/0}$ for a hybrid mouse obtained by crossing a mouse with a chimeric prion protein gene (MHu2M) with a mouse with both alleles of the endogenous prion protein gene disrupted;

TTR for transthyretin;

FVB for a standard inbred strain of mice often used in the production of transgenic mice since eggs of FVB mice are relatively large and tolerate microinjection of exogenous DNA relatively well;

[PrP$_\beta$]—concentration of prion protein in β-sheet conformation;

[βA4$_\beta$]—concentration of βA4 in β-sheet conformation;

[DRC]—concentration of a disease related conformation of a protein.

GENERAL ASPECTS OF THE INVENTION

Some proteins such as the protein expressed by the PrP gene have more than one conformational shape. For example a PrP protein may assume its cellular form, i.e. PrP$^c$ form or its scrapies form, i.e. PrP$^{Sc}$ form. One form of the protein is harmless (e.g. PrP$^c$) whereas another form of the protein is pathogenic (e.g. PrP$^{Sc}$). When the constricted, pathogenic form of the protein such as PrP$^{Sc}$ is present in an animal in very small amounts the animal is not showing symptoms of disease. However, the animal will develop a disease related to the pathogenic form of the protein—e.g. develop a prion disease. To avoid transmission of disease it is important to determine if a sample derived from an animal is infected with the disease form of a protein, e.g. has PrP$^{Sc}$ in its brain tissue. The present invention is useful with respect to (1) concentrating the pathogenic form of a protein that is present in a sample, (2) eliminating the pathogenic form of the protein from the sample and/or (3) reducing the concentration of the pathogenic form of the protein in a material to a level such that the material is rendered "non-infectious."

The presence of a pathogenic form of a protein (e.g. PrP$^{Sc}$) can be determined in a number of ways. For example a sample to be tested can be used to innoculate transgenic mice which have been genetically engineered to be susceptible to the pathogenic protein being tested for—see U.S. Pat. No. 5,565,186. Alternatively, the sample can be treated to expose epitopes and tested against antibodies which bind to the treated protein—see U.S. patent application Ser. No. 08/804,536 filed Feb. 21, 1997 now U.S. Pat. No. 5,891,641 issued Apr. 6, 1999 and the monoclonal antibody 263K 3F4, produced by cell line ATCC HB9222 deposited Oct. 8, 1996 and U.S. Pat. No. 4,806,627 issued Feb. 21, 1986.

Regardless of the type of method used to assay for the presence of a pathogenic form of a protein (e.g. PrP$^{Sc}$) the assay results can be improved if the concentration of the pathogenic protein in the sample being tested can be increased. In particular, assay results can be improved if the concentration of the pathogenic form of the protein in the sample can be increased relative to the concentration of the non-pathogenic form of the protein in the sample. This is particularly important because the concentration of the non-pathogenic form of the protein is generally substantially greater (10 fold or more) than the concentration of the pathogenic form. The present invention makes it possible to precipitate out and thereby concentrate the pathogenic form of a protein such as PrP$^{Sc}$. Thus, the concentrated protein can be assayed thereby enhancing the sensitivity of any assay for the protein. Further, the invention can be used to reduce the concentration of a pathogenic form of a protein in a material to a level such that a material which was infectious is rendered non-infectious.

PROCEDURES IN GENERAL

Any type of sample can be processed using the present invention in order to concentrate the constricted, pathogenic form of a protein. However, proteins having a constrictive and a relaxed conformation are generally found in brain tissue. Thus, the invention is described using brain tissue as the starting material from which the pathogenic protein is concentrated. Although the invention could be applied to concentrating a constricted form of any protein having a constricted and relaxed form, the invention is described specifically with respect to concentrating the pathogenic form of a PrP protein, i.e. concentrating PrP$^{Sc}$ which is present in brain tissue along with PrP$^c$.

A sample to be treated should be in a liquid flowable form at room temperature (15° C. to 30° C.). Brain tissue is homogenized and diluted with a saline solution such as a phosphate buffered saline solution. The solution should have a pH of about 6.4 to 8.4, preferably 7.4, not contain magnesium or calcium and preferably comprise about 4% (w/v) of sodium dodecylsarcosinate (Sarcosyl). The solution is added to the brain homogenate in a ratio of 1:5 to 5:1 and preferably in a ratio of about 1:1 and mixed at room temperature.

The next step is the most important in the process of the invention. A complexing agent is added to the sample which agent forms a complex with or somehow binds preferentially with or exclusively to any constricted (generally a pathogenic form) of the protein present in the sample. Phosphotungstic acid may be and preferably is added in the form of a salt—e.g. a stock solution containing 4% sodium phosphotungstate (NaPTA) and 170 mM MgCl$_2$, pH 7.4 is added to obtain a final concentration of PTA of about 0.2 to 0.3%. However, the PTA may be added so as to obtain lower or higher concentrations of PTA it being understood that higher concentrations can be used but are not generally needed to obtain the desired effect of forming complexes with any PrP$^{Sc}$ present. After the PTA is added the sample is subjected to a sufficient amount of mixing over a period of time sufficient to allow substantially all the PrP$^{Sc}$ in the sample to complex with the PTA. For example, the sample could be incubated at about 30° C. to 45° C. (preferably 37° C.) over a period of from about 1 to 16 hours on a rocking platform. The PTA (which is the complexing agent) forms a complex with the PrP$^{Sc}$ (which is the constricted conformation of the protein). The PTA/PrP$^{Sc}$ complex formed will have a higher density than PrP$^{Sc}$ alone. The complexing agent and protein may form any type of complex with equal or unequal numbers of each of the molecules. What is important is that complex formed can be separated away from the rest of the composition by some means.

Next small portions of the sample (e.g. 1 ml portions) are placed in containers such as Eppendorf tubes and centrifuged—e.g. at about 14,000 g using a table top centrifuge for about 30 minutes. It will be understood by those skilled in the art that lower and higher speeds can be used over shorter or longer times to obtain the desired effect of settling out the heavy complexes of $PrP^{Sc}/PTA$ formed.

Certain enzymes are capable of degrading protein in one form but not another. For example, Proteinase K degrades $PrP^c$ but not $PrP^{Sc}$. The Proteinase K is added to the sample (before or after centrifuging) in that a low concentration of Proteinase K generally increases the efficiency of precipitation of $PrP^{Sc}/PTA$ and thereby increasing the density differential between $PrP^c$ (degraded) and $PrP^{Sc}$ (complexed with PTA).

After centrifuging, the supernatant is decanted away leaving a precipitated pellet. The pellet is resuspended in water preferably containing protease inhibitors, e.g. PMSF 0.5 mM; Aprotinin and Leupeptin, 2 μg/ml each. The suspension is centrifuged and the content of the resulting pellet is reduced 100-fold. Typically, if the sample was taken from an animal that died from a prion disease the resulting pellet will contain about 40 to 60% $PrP^{Sc}$ or PrP 27–30 which is a core component of $PrP^{Sc}$ not digested by Proteinase K.

The process of the invention produces a suspension wherein the $PrP^{Sc}$ or other pathogenic protein remaining is stained with the PTA used. This is desirable in that further analysis by a number of methods requires staining. Thus, the product obtained can be directly subjected to SDS PAGE, Western blots, dot blots or a differential conformational assay as described in U.S. patent application Ser. No. 08/804,536 filed Feb. 21, 1997.

The method of the invention can be used for (1) concentrating any $PrP^{Sc}$ in a sample for further analysis and/or (2) removing $PrP^{Sc}$ from a material to render the material non-infectious. If rendering the material non-infectious is all that is required, the method of the invention can be simplified. The material is liquified and brought into contact with the appropriate complexing agent. After complexes have been allowed to form centrifugation is used to precipitate out the complexes and thereby render the remaining material non-infectious. Further processing of the precipitated material is not needed but may be carried out to obtain desired information. Such processing is described below.

FURTHER ANALYSIS

After concentrating the constricted conformation of the protein with the complexing agent and centrifuging as described above, the sample can and preferably is subjected to further analysis. One such analysis protocol involves contacting a first portion of the sample with a binding partner, such as an antibody which binds $PrP^c$ and treated $PrP^{Sc}$, said binding partner having a higher affinity for the first conformation (e.g. $PrP^c$) than the second constricted conformation (e.g. $PrP^{Sc}$), and determining a first concentration. A suitable antibody is 3F4 disclosed in U.S. Pat. No. 4,806,627 issued Feb. 21, 1986. A second portion of the sample is treated to increase binding affinity of the second constricted conformation to the binding partner, for example treating to expose $PrP^{Sc}$ epitopes. The treatment can involve heat, pressure and/or chemical denaturation of the constricted pathogenic protein (e.g., $PrP^{Sc}$) sufficient to convert 2% or more of the constricted form to a form which binds the binding partner. The treated second portion of the sample is contacted with the binding partner to determine a second concentration, i.e., the concentration of particles which now bind the binding partner. An increase should be observed if the original sample included protein in a constricted conformation and that protein was converted to a different conformation due to the treatment. After the second concentration is determined, it is adjusted to compensate for increased affinity of the protein in the first conformation for the binding partner resulting from the treating. Finally, the first concentration is compared with the adjusted concentration to determine the presence of protein in the second conformation.

The first concentration and the second concentration are preferably determined using time-resolved, dissociation-enhanced fluorescence. Preferably, the second concentration is higher than the first concentration in the sample, with the second concentration being $1 \times 10^3$ particles/ml or less. The protein in the sample is preferably selected from the group consisting of βA4 protein, PrP protein, and transthyretin. Details regarding methods of carrying out the further analysis described above are contained within U.S. patent application Ser. No. 08/804,536 filed Feb. 21, 1997 now U.S. Pat. No. 5,891,641 issued Apr. 6, 1994 and U.S. application attorney docket number 06510/081001 filed Feb. 20, 1998 entitled "Assay for Disease Related Conformation of a Protein"—both of which are incorporated by reference to disclose and describe such methods.

DISEASES ASSOCIATED WITH INSOLUBLE PROTEINS

Much of the disclosure and the specific examples provided herein relate to the use of the invention in connection with concentrating $PrP^{Sc}$ in the sample. However, as indicated above, the invention can be applied to determining the presence of any protein which assumes two or more different shapes, one of which is constricted (generally associated with the disease) and one which is relaxed (generally not a disease conformation). The following is a non-limiting list of diseases with associated proteins which assume two or more different conformation—a constricted and a relaxed conformation.

| Disease | Insoluble Proteins |
| --- | --- |
| Alzheimer's Disease | APP, Aβ peptide, α1-antichymotrypsin, tan, non-Aβ component |
| Prion diseases, Creutzfeld Jakob disease, scrapie and bovine spongeform encephalopathy | $PrP^{Sc}$ |
| ALS | SOD and neurofilament |
| Pick's disease | Pick body |
| Parkinson's disease | Lewy body |
| Diabetes Type 1 | Amylin |
| Multiple myeloma-- plasma cell dyscrasias | IgGL-chain |
| Familial amyloidotic polyneuropathy | Transthyretin |
| Medullary carcinoma of thyroid | Procalcitonin |
| Chronic renal failure | $β_2$--microgobulin |
| Congestive heart failure | Atrial natriuretic factor |
| Senile cardiac and systemic amyloidosis | Transthyretin |
| Chronic inflammation | Serum amyloid A |
| Atherosclerosis | ApoA1 |
| Familial amyloidosis | Gelsolin |

It should be noted that the insoluble proteins listed above each include a number of variants or mutations which are intended to be encompassed by the present invention. Known pathogenic mutations and polymorphisms in the PrP gene related to prion diseases are given below and the sequences of human, sheep and bovine are given in U.S. Pat. No. 5,565,186, issued Oct. 15, 1996.

MUTATION TABLE

| Pathogenic human mutations | Human Polymorphisms | Sheep Polymorphisms | Bovine Polymorphisms |
|---|---|---|---|
| 2 octarepeat insert | Codon 129 | Codon 171 | 5 or 6 octarepeats |
|  | Met/Val | Arg/Glu |  |
| 4 octarepeat insert | Codon 219 | Codon 136 |  |
|  | Glu/Lys | Ala/Val |  |
| 5 octarepeat insert |  |  |  |
| 6 octarepeat insert |  |  |  |
| 7 octarepeat insert |  |  |  |
| 8 octarepeat insert |  |  |  |
| 9 octarepeat insert |  |  |  |
| Codon 102 Pro-Leu |  |  |  |
| Codon 105 Pro-Leu |  |  |  |
| Codon 117 Ala-Val |  |  |  |
| Codon 145 Stop |  |  |  |
| Codon 178 Asp-Asn |  |  |  |
| Codon 180 Val-Ile |  |  |  |
| Codon 198 Phe-Ser |  |  |  |
| Codon 200 Glu-Lys |  |  |  |
| Codon 210 Val-Ile |  |  |  |
| Codon 217 Asn-Arg |  |  |  |
| Codon 232 Met-Ala |  |  |  |

It should also be noted that while such proteins have two different 3-dimensional conformations, they have the same amino acid sequence. One conformation is associated with disease characteristics and is generally insoluble (e.g., $PrP^{Sc}$) whereas the other conformation is not associated with disease characteristics (e.g., $PrP^{c}$) and is soluble.

SPECIFICS OF A PrP PROTEIN

The major component of purified infectious prions ($PrP^{Sc}$) is the core which is designated PrP 27–30. It is this proteinase K resistant core of the larger native protein $PrP^{Sc}$ which signifies the disease causing form and distinguishes this form from the ubiquitous cellular protein $PrP^c$. $PrP^{Sc}$ is found only in scrapie infected cells whereas $PrP^c$ is present in both infected and uninfected cells implicating $PrP^{Sc}$ as the major, if not sole, component of infectious prion particles.

Since both $PrP^c$ and $PrP^{Sc}$ are encoded by the same single copy gene, great effort has been directed toward unraveling the mechanism by which $PrP^{Sc}$ is derived from $PrP^c$. Central to this goal has been the characterization of physical and chemical differences between these two molecules. Properties distinguishing $PrP^{Sc}$ from $PrP^c$ include low solubility [Meyer, McKinley et al. (1986) *Proc Natl Acad Sci USA* 83:2310–2314], poor antigenicity [Kascsak, Rubenstein et al. (1987) *J Virol* 61:3688–3693; Serban, Taraboulos et al. (1990) *Neurology* 40:110–117], protease resistance [Oesch, Westaway et al. (1985) *Cell* 40:735–746], and polymerization of PrP 27–30 into rod shaped aggregates which are very similar, on the ultrastructural and histochemical levels, to the PrP amyloid plagues seen in scrapie diseased brains [Prusiner, McKinley et al. (1983) *Cell* 35:349–358]. To date, attempts to identify any post-transitional chemical modifications in $PrP^c$ that lead to its conversion to $PrP^{Sc}$ have proven fruitless [Stahl, Baldwin et al. (1993) Biochemistry 32: 1991–2002]. Consequently, it has been proposed that $PrP^c$ and $PrP^{Sc}$ are in fact conformational isomers of the same molecule.

Conformational description of PrP using conventional techniques has been hindered by problems of solubility and the difficulty in producing sufficient quantities of pure protein. However, $PrP^c$ and $PrP^{Sc}$ are conformationally distinct. Theoretical calculations based upon the amino acid sequences of PrP proteins from several species have predicted four putative helical motifs in the molecule. Experimental spectroscopic data would indicate that in $PrP^c$ these regions adopt α-helical arrangements, with virtually no β-sheet [Pan, Baldwin et al. (1993) *Proc Natl Acad Sci USA* 90:10962–10966; Safar, Roller et al. (1995) Research Advances in Alzheimer's Disease and Related Disorders: 775–781]. In dramatic contrast, in the same study it was found that $PrP^{Sc}$ and PrP 27–30 posses significant β-sheet content, which is typical of amyloid proteins [Pan, Baldwin et al., supra; Safar, Roller et al. (1993) *J Biol Chem* 268:20276–20284]. Moreover, studies with extended synthetic peptides, corresponding to PrP amino acid residues 90–145, have demonstrated that these truncated molecules may be converted to either α-helical or β-sheet structures by altering their solution conditions. The transition of $PrP^c$ to $PrP^{Sc}$ requires the adoption of β-sheet structure by regions that were previously α-helical. It is believed that the β-sheet structural configuration does not provide exposed epitopes which bind well to antibodies, whereas an α-helical structured configuration does provide exposed epitopes which have a higher affinity for antibodies. Because $PrP^{Sc}$ does not have significant exposed epitopes it is very difficult to generate antibodies which bind to $PrP^{Sc}$ making it difficult to determine if $PrP^{Sc}$ is present in a sample or to remove $PrP^{Sc}$ from a sample. The present invention addresses these difficulties.

ANTIBODIES

The complexing agent of the invention may be an antibody which antibody may be bound to another component (e.g. a high density metal). That antibody may bind to $PrP^{Sc}$, e.g. the antibody disclosed in U.S. patent application Ser. No. 08/713,939, filed Sep. 13, 1996 now U.S. Pat. No. 5,846,533 issued Dec. 8, 1998. However, in order to remove $PrP^c$ present in the sample, an antibody which binds selectively or exclusively to $PrP^c$ may be used. Such an antibody is disclosed in U.S. Pat. No. 4,806,627, issued Feb. 21, 1989, disclosing monoclonal antibody 263K 3F4, produced by cell line ATCC HB9222 deposited on Oct. 8, 1986, which is incorporated herein by reference. The cell line producing the antibody can be obtained from the American Type Culture Collection, 12301 Parklawn Drive, Rockville, Md. 20852.

In general, scrapie infection fails to produce an immune response, with host organisms being tolerant to $PrP^{Sc}$ from the same species. Antibodies which bind to either $PrP^c$ or $PrP^{Sc}$ are disclosed in WO97/10505, published Mar. 20, 1997. Any antibody binding to $PrP^c$ and not to $PrP^{Sc}$ can be used, and those skilled in the art can generate such using known procedures, e.g., see methods of producing phage display antibody libraries in U.S. Pat. No. 5,223,409. Polyclonal anti-PrP antibodies have though been raised in rabbits following immunization with large amounts of formic acid or SDS-denatured SHaPrP 27–30 [Bendheim, Barry et al. (1984) *Nature* 310:418–421; Bode, Pocchiari et al. (1985) *J Gen Virol* 66:2471–2478; Safar, Ceroni et al. (1990) *Neurology* 40:513–517]. Similarly, a handful of anti-PrP monoclonal antibodies against PrP 27–30 have been produced in mice [Barry and Prusiner (1986) *J Infect Dis* 154:518–521; Kascsak, Rubenstein et al. (1987) *J Virol* 61:3688–3693]. These antibodies were generated against formic acid- or SDS-denatured PrP 27–30 and are able to recognize native $PrP^c$ and treated or denatured $PrP^{Sc}$ from both SHa and humans equally well, but do not bind to MoPrP. Not surprisingly, the epitopes of these antibodies were mapped to regions of the sequence containing amino acid differences between SHa- and MoPrP [Rogers, Yehiely et al. (1993) *Proc Natl Acad Sci USA* 90:3182–3186].

It is not entirely clear why many antibodies of the type described in the above cited publications will bind to PrP$^c$ and treated or denatured PrP$^{Sc}$ but not to native PrP$^{Sc}$. Without being bound to any particular theory it is believed that such may take place because epitopes which are exposed when the protein is in the PrP$^c$ conformation are unexposed or partially hidden in the PrP$^{Sc}$ configuration—where the protein is relatively insoluble and more compactly folded together.

For purposes of the invention an indication that no binding occurs means that the equilibrium or affinity constant $K_a$ is $10^6$ 1/mole or less. Further, binding will be recognized as existing when the $K_a$ is at $10^7$ 1/mole or greater, preferably $10^8$ 1/mole or greater. The binding affinity of $10^7$ 1/mole or more may be due to (1) a single monoclonal antibody (i.e., large numbers of one kind of antibodies) or (2) a plurality of different monoclonal antibodies (e.g., large numbers of each of five different monoclonal antibodies) or (3) large numbers of polyclonal antibodies. It is also possible to use combinations of(1)–(3). Selected preferred antibodies will bind at least 4-fold more avidly to the treated or denatured $PrP^{Sc}$ forms of the protein when compared with their binding to the native conformation of $PrP^{Sc}$. The four fold differential in binding affinity may be accomplished by using several different antibodies as per (1)–(3) above and as such some of the antibodies in a mixture could have less than a four fold difference.

A variety of different methods may be used with one or more different antibodies. Those skill in the art will recognize that antibodies may be labeled with known labels and used with currently available robotics, sandwich assays, electronic detectors, flow cytometry, and the like. Further, the antibodies may be bound to denser components directly or via other intermediates such as anti-antibodies.

ANTIBODY/ANTIGEN BINDING FORCES

The forces which hold an antigen and antibody together are in essence no different from non-specific interactions which occur between any two unrelated proteins, i.e., other macromolecules such as human serum albumin and human transferrin. These intermolecular forces may be classified into four general areas which are (1) electrostatic; (2) hydrogen bonding; (3) hydrophobic; and (4) Van der Waals. Electrostatic forces are due to the attraction between oppositely charged ionic groups on two protein side-chains. The force of attraction (F) is inversely proportional to the square of the distance (d) between the charges. Hydrogen bonding forces are provided by the formation of reversible non-covalent hydrogen bridges between highly electronegative elements (F, O, N, Cl), such as in the hydrophilic groups —OH, —$NH_2$, and —COOH. These forces are largely dependent upon close positioning of two molecules carrying these groups. Hydrophobic forces operate in the same way that oil droplets in water merge to form a single large drop. Accordingly, non-polar, hydrophobic groups such as the side-chains on valine, leucine and phenylalanine tend to associate in an aqueous environment. Lastly, Van der Waals are forces created between molecules which depend on interaction between the external electron clouds. All the above interactions depend on complementarity between conformation of the antigen and antibody recognition site.

Further information regarding each of the different types of forces can be obtained from "Essential Immunology edited by I. M. Roitti (6th Edition) Blackwell Scientific Publications, 1988. With respect to the present invention, useful antibodies exhibit some or all of these forces. It is by obtaining an accumulation of these forces in larger amounts that it is possible to obtain an antibody which has a high degree of affinity or binding strength to the PrP protein and in particular an antibody which has a high degree of binding strength to the configuration of $PrP^c$ and/or the random coil configuration obtained by treating any β-sheet PrP protein in situ.

EXAMPLES

The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

EXAMPLE 1

Purification of Hamster $PrP^c$ from Normal and $PrP^{Sc}$ From Scrapie Infected Hamster Brains The $PrP^c$ protein can be purified as described in Pan, Stahl et al. (1992) *Protein Sci* 1:1343–1352; Pan, Baldwin et al. (1993) *Proc Natl Acad Sci USA* 90:10962–10966. Protein content can be determined by amino acid analysis. The purity of $PrP^c$ protein, can be determined on SDS PAGE followed by silver staining and Western.

Standard Syrian hamster $PrP^{Sc}$ can be purified from a standard pool of scrapie strain Sc237 infected hamster brains as described in Turk, Teplow et al. (1988) *Eur J Biochem* 176:21–30. The infectivity of this standard, as determined by an incubation time assay on Syrian hamsters after intracerebral inoculation, should be $10^{7.3}$ $ID_{50}$/ml and specific infectivity $10^{8.2}$ $ID_{50}$/mg of $PrP^{Sc}$ protein. However, the specific infectivity may vary from lot to lot $\pm 10^{0.5}$ $ID_{50}$/mg. The protein content can be determined by BCA assay using Bovine serum albumin as a standard. The preparation can be considered homogeneous with one major band on SDS PAGE after silver staining and Western Blots. The PrP proteins of the brain of other animals can be obtained in the same manner.

EXAMPLE 2

Isolation of $PrP^{Sc}$ from Bovine Brain $PrP^{Sc}$ is isolated from a fresh brain sample of a cow that exhibited symptoms of a neurological disorder consistent with the presence of $PrP^{Sc}$. Approximately 10 g of brain tissue is used to produce a homogenate. The brain tissue is flash-frozen in liquid nitrogen, and then homogenized using a standard mortar and pestle technique to dissociate the tissue for further extraction procedures. Phosphate buffered saline (PBS) pH 7.4 containing 4% (w/v) sodium dodecylsarcosinate (sarcosyl), an ionic surfactant, is added to the brain homogenate in a 1:5 (v/v) ratio to the brain homogenate. A solution of 4% sodium phosphotungstic acid (PTA) and 170 mM $MgCl_2$, pH 7.4, is added to the buffered homogenate solution to a final concentration of 0.2% PTA. The sample is exposed to the PTA for 16 hours at 30° C. on a rocking platform. At the end of 16 hours, Proteinase K is added to the solution providing a final concentration of 25 mg/ml, and the sample is incubated for one additional hour at 37° C. The addition of proteinase K generally increases the efficiency of the precipitation of PrP$^{Sc}$, in part by degrading other remaining proteins including PrP$^c$.

Following incubation, the sample is transferred to 1.5 ml sterile tubes, with approximately 1 ml aliquots of the PTA-homogenate solution per tube. The sample is centrifuged at 10,000 g in a table top centrifuge (Eppendorf) for 40 minutes at room temperature. The supernatant is decanted from the tubes, and each pellet is resuspended in sterile water to the desired overall protein concentration. Protease inhibitors are added to the solution: PMSF to a concentration 0.5 mM, Aprotinin to a final concentration of 2 mg/ml, and Leupeptin to a final concentration of 2 mg/ml. The protease inhibitors protect the sample from degradation under certain storage conditions. An aliquot of protein for current use is stored at 4° C. The remaining protein is aliquoted, and stored at −20° C.

The total protein content of the pellet is reduced 100 fold as compared to similar procedures known in the art. The PrP$^{Sc}$ or PrP 27–30 content of this pellet represents approximately 40–60% of the total protein. This procedure thus results in a protein sample highly enriched in PrP$^{Sc}$ protein species.

EXAMPLE 3

Isolation of PrP$^{Sc}$ from Human Brain

PrP$^{Sc}$ is isolated from brain samples of a deceased individual suspected of being affected with a prion-based neurological disorder. Approximately 5 g of human brain tissue is used to produce a homogenate. The homogenate is produced using a dounce homogenizer to dissociated the tissue for protein extraction. A solution of 0.24 mM Triton-X, a non-ionic surfactant, in PBS pH 7.4 is added to a final 1:1 (v/v) ratio. A solution of 4% sodium phosphotungstic acid (PTA) and 170 mM MgCl$_2$, pH 7.4, is added to the buffered homogenate solution to a final concentration of 0.3% PTA. The sample is exposed to the PTA for 8 hours at 37° C. on a rocking platform.

Following incubation, the sample is transferred to 2.0 ml sterile tubes, with approximately 1 ml aliquots of the PTA-homogenate solution per tube. The sample is centrifuged at 14,000 g in a table top centrifuge (Brinkmann) for 30 minutes at room temperature. The supernatant is decanted from the tubes, and each pellet is resuspended in a 25 mg/ml proteinase K solution. The tubes are incubated for one additional hour, rocking, at 37° C. The sample is again centrifuged at 14,000 g in a table top centrifuge for 30 minutes at room temperature. The supernatant is decanted, and the sample resuspended in 100 ml of sterilized water. Concentration can be determined using spectrophotometric techniques. The PrP$^{Sc}$ or PrP 27–30 content of this pellet represents approximately 40–60% of the total protein.

EXAMPLE 4

Isolation of PrP$^{Sc}$ from Sheep Brain

A brain sample from a sheep exhibiting neurological disorders is isolated and homogenized using a Polytron automated homogenizer. Approximately 1 gram of protein is homogenized in this fashion. PBS pH 7.4 containing 1% (w/v) sodium dodecyl sulfate (SDS) is added to the brain homogenate in a 5:1 (v/v) ratio. A solution of 4% sodium phosphotungstic acid (PTA) and 170 mM MgCl$_2$, pH 7.4, is added to the buffered homogenate solution to a final concentration of 0.25% PTA. The sample is exposed to the PTA for 1 hour at 45° C. on a rocking platform.

Following incubation, the sample is transferred to 1.5 ml sterile tubes, with approximately 1 ml aliquots of the PTA-homogenate solution per tube. The sample is centrifuged at 20,000 g in a table top centrifuge (Eppendorf) for 20 minutes at room temperature. The supernatant is decanted from the tubes, and each pellet is resuspended in sterile water to the desired overall protein concentration. An aliquot of protein for current use is stored at 4° C. The remaining protein is aliquoted, and stored at −20° C. The PrP$^{Sc}$ or PrP 27–30 content of this pellet represents approximately 40–60% of the total protein.

EXAMPLE 5

Rendering infectious material non-infectious

Samples of scrapie-infected 5% (w/v) Syrian hamster brain homogenates, prepared in PBS, pH 7.4 (no Mg or Ca) and containing 2% (w/v) of sodium dodecylsarcosinate (Sarcosyl), were mixed with stock solution containing 4% sodium phosphotungstate (NaPTA) and 170 mM MgCl$_2$, pH 7.4. Samples containing final 0.2–0.3% (w/v) of PTA were incubated for 1–16 hrs at 37° C. on a rocking platform.

Eppendorf tubes containing typically 1 ml samples were centrifuged at 14,000 g in a table top centrifuge (Eppendorf) for 30 min at room temperature. The supernatant was decanted and pellet resuspended in H$_2$O containing protease inhibitors (PMSF 0.5 mM; Aprotinin and Leupeptin, 2 μg/ml each). The starting brain homogenate, the homogenate containing PTA, the supernatant of PTA precipitated brain homogenate, and resuspended pellet were assayed for prion infectivity by incubation time assay in Syrian hamsters. The results are presented as titer/ml in FIG. 1.

Figure 1:
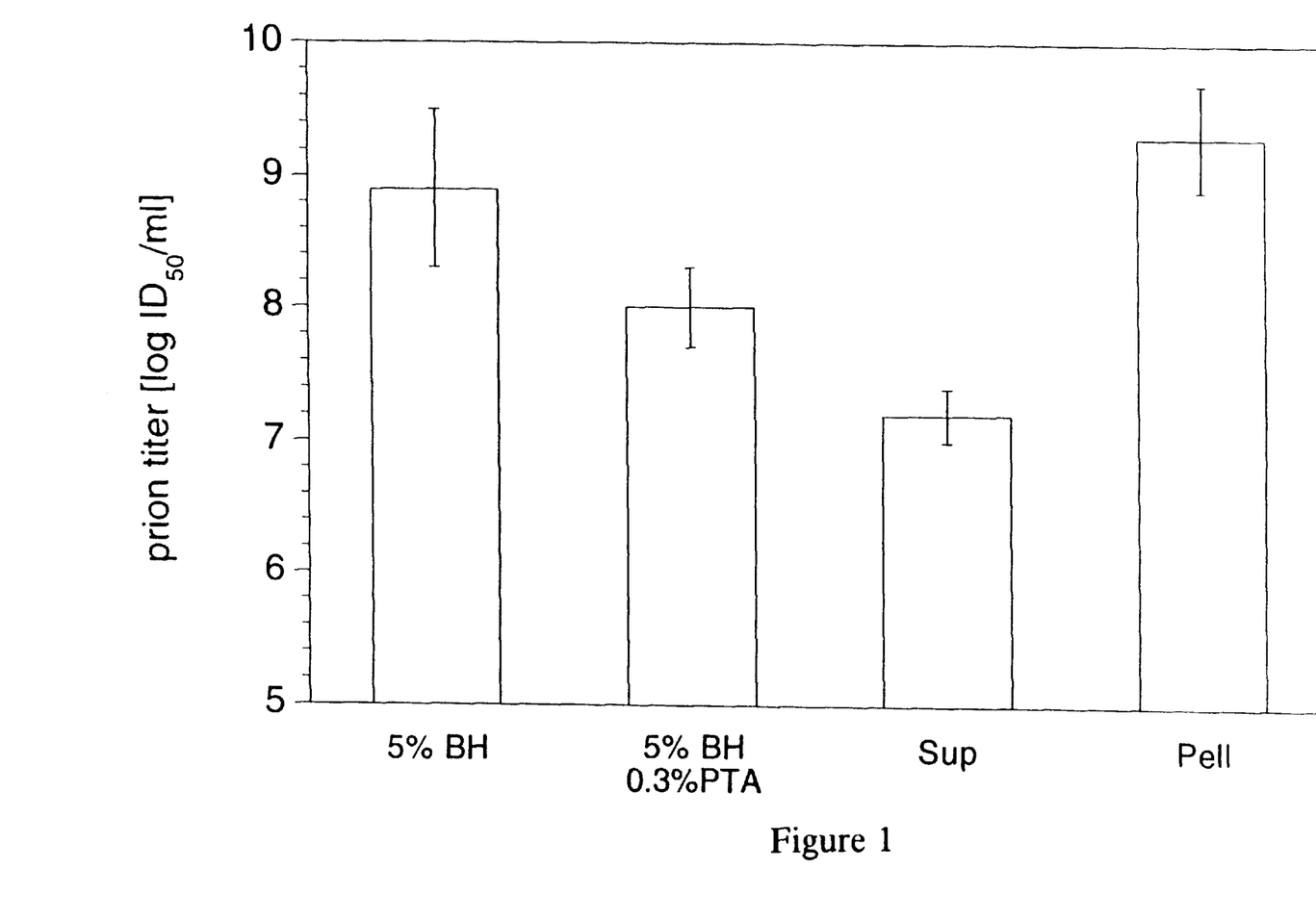
FIG. 1 is a bar graph of the prion titer (log $ID_{50}$/ml) for four different samples tested.

Prion infected material is rendered non-infectious by using phosphotungstic acid to precipitate infectious prions from scrapie-infected Syrian hamster brain homogenates. Brain homogenate in final concentration of 5%, containing 2% Sarcosyl, was prepared from brains of scrapie-infected (isolate Sc237) Syrian hamsters (LVG/LAK), mixed with final 0.3% of phosphotungstic acid (5% BH/0.3% PTA), and spun for 30 min at 14,000 g, and separated into pellet (Pell) and supernatant (Sup)—as shown in FIG. 1. PTA precipitated 99% of the infectious prions presented in the material in the pellet. Columns and bars representing data obtained from independent experiments are shown in FIG. 1.

The instant invention is shown and described herein what is considered to be the most practical, and preferred embodiments. It is recognized, however, that departures may be made therefrom which are within the scope of the invention, and that obvious modifications will occur to one skilled in the art upon reading this disclosure.

What is claimed is:

1. A method of concentrating a constricted form of a protein which occurs in a constricted conformation and a relaxed conformation, comprising adding a complexing agent to a sample wherein the complexing agent selectively complexes with the constricted conformation of the protein;

mixing the complexing agent with the sample for a time sufficient to form complexes between the agent and a constricted form of a protein;

centrifuging the sample containing the complexes; and treating the sample with a protease which selectively degrades the relaxed conformation of the protein, wherein the treating is carried out prior to or after centrifuging.

2. The method of claim 1, wherein the constricted form of the protein is associated with a pathogenic disorder; and further wherein the sample is from the brain tissue of an animal suspected of having a central nervous system disorder; and still further wherein the mixing is carried out for a time and in a manner which evenly distributes the complexing agent in the sample.

3. The method of claim 1, wherein the centrifuging is carried out at about 10,000 to 20,000 g for about 10 minutes or more, the sample is homogenized brain tissue containing $PrP^{Sc}$ and the complexing agent is phosphotungstic acid.

4. The method of claim 1, further comprising:
decanting away a supernatant obtained after centrifuging;
obtaining a pellet resulting from the centrifuging and decanting;
resuspending the pellet in water and protease inhibitor to obtain a suspension; and analyzing the suspension.

5. The method of claim 4, wherein the analyzing is carried out using a process selected from the group consisting of: an SDS PAGE, a Western blot, a dot blot, and visualization via electron microscopy.

6. The method of claim 1, wherein the protein is a PrP protein, and the protease is Proteinase K.

7. The method of claim 6, wherein the treating is carried out prior to the centrifuging.

8. A method of concentrating $PrP^{Sc}$ present in a sample, comprising:
adding phosphotungstic acid or a salt thereof to a sample;
mixing the phosphotungstic acid or salt thereof with the sample; and
centrifuging the sample containing the phosphotungstic acid or salt thereof to precipitate out and thereby concentrate $PrP^{Sc}$ in the sample.

9. The method of claim 8, wherein the phosphotungstic acid is added in an amount so as to provide a concentration of about 0.05 to 10% of phosphotungstic acid, and wherein the mixing is carried out for a time and in a manner which evenly distributes the phosphotungstic acid in a sample.

10. The method of claim 8, where the centrifuging is carried out about 10,000 to 20,000 g for about 10 minutes or more.

11. The method of claim 8, further comprising:
treating the sample with Proteinase K.

12. The method of claim 8, further comprising:
decanting away supernatant obtained after centrifuging; and
obtaining a pellet resulting from the centrifuging and decanting.

13. The method of claim 12, further comprising:
resuspending the pellet in water and protease inhibitor to obtain a suspension; and
analyzing the suspension.

14. The method of claim 13, wherein the analyzing is carried out using a process selected from the group consisting of an SDS PAGE, a Western blot, a dot blot, and visualization via electron microscopy.

15. The method of claim 8, wherein the sample is a sample of homogenized brain tissue from an animal suspected of having $PrP^{Sc}$ in its brain tissue.

16. The method of claim 8, wherein the sample is a pharmaceutical composition comprised of a pharmaceutically active drug and pharmaceutically acceptable carrier.

17. A method of rendering a sample non-infectious wherein the sample comprises a protein which occurs in a first, infectious, constricted conformation and a second, non-infectious, relaxed conformation, comprising:
adding a complexing agent to the sample wherein the complexing agent selectively complexes with the constricted conformation and is added in an amount such that complexing agent molecules are available for all molecules of constricted conformation of the protein present in the sample;
mixing the complexing agent with the sample for a time and in a manner which evenly distributes the complexing agent in the sample and allows complexes to be formed between molecules of complexing agent and molecules of the constricted conformation of the protein;
centrifuging the sample for a time and at a speed to precipitate complexes from a sample supernatant formed by centrifuging;
separating the precipitated complexes from the sample thereby rendering the sample non-infectious.

18. The method of claim 17, wherein the protein is PrP and the constricted conformation is $PrP^{Sc}$ and the relaxed conformation is $PrP^{c}$.

19. The method of claim 17, wherein the complexing agent is phosphotungstic acid or a salt thereof.

20. The method of claim 17, further comprising:
treating the sample with a protease which selectively degrades the relaxed form of the protein.

* * * * *

UNITED STATES PATENT AND TRADEMARK OFFICE
CERTIFICATE OF CORRECTION

PATENT NO: 5,977,324
DATED: November 2, 1999
INVENTOR(S): Stanley B. Prusiner; Jiri G. Safar It is certified that error appears in the above-identified patent and that said Letters Patent is hereby corrected as shown below:

Col. 1, beneath the title, please insert the following:

--GOVERNMENT RIGHTS
The United States Government may have certain rights in this application pursuant to Grants AG02132 and NS14069, awarded by the National Institutes of Health.--

Signed and Sealed this

Nineteenth Day of September, 2000

Attest:

Q. TODD DICKINSON

*Attesting Officer*          *Director of Patents and Trademarks*